United States Patent [19]

Middleton

[11] Patent Number: 5,620,771

[45] Date of Patent: Apr. 15, 1997

[54] FABRIC OF COTTON/NYLON AND ELASTOMERIC NEOPRENE

[75] Inventor: Nigel J. Middleton, Cornwall, Great Britain

[73] Assignee: Micro Thermal Systems, Limited, Cornwall, United Kingdom

[21] Appl. No.: 483,409

[22] Filed: Jun. 7, 1995

Related U.S. Application Data

[63] Continuation of Ser. No. 934,620, Aug. 27, 1992.

[30] Foreign Application Priority Data

Feb. 28, 1990 [GB] United Kingdom .................. 9004428

[51] Int. Cl.⁶ ........................................ B32B 3/10
[52] U.S. Cl. ........................ 428/131; 428/139; 428/138
[58] Field of Search ................................ 428/131, 137, 428/138

[56] References Cited

U.S. PATENT DOCUMENTS 4,636,424  1/1987  Amemiya et al. .
4,846,164  7/1989  Martz ......................................... 128/155

FOREIGN PATENT DOCUMENTS

| 0018684 | 11/1980 | European Pat. Off. ........ A41B 13/02 |
| 0052403 | 5/1982 | European Pat. Off. ........ A61F 13/18 |
| 2917478 | 9/1980 | Germany ......................... B32B 5/18 |
| 1237127 | 6/1971 | United Kingdom ............. B32B 3/24 |
| 1235224 | 6/1971 | United Kingdom ............. B26F 1/26 |
| 1267712 | 3/1972 | United Kingdom . |
| 2046171 | 11/1980 | United Kingdom ............. B32B 5/04 |
| 1598948 | 8/1981 | United Kingdom ........... B32B 31/12 |
| 2175845 | 12/1986 | United Kingdom ........... B29C 59/00 |
| 2202873 | 10/1988 | United Kingdom ............. D04H 3/04 |

Primary Examiner—Thurman K. Page
Assistant Examiner—Kathryne E. Shelborne
Attorney, Agent, or Firm—Lowe, Price, LeBlanc & Becker

[57] ABSTRACT

There is provided a laminated fabric comprising a sheet portion of a material compatible with human skin, the being adhered to a second sheet formed of a substantially impermeable material having perforations provided therethrough, each perforation having at least one relatively wide region and at least one relatively narrow region along its length to define an internal chamber open to a first ("inner") side of the sheet and sufficiently closed to the other ("outer") side of the sheet to permit air passing from the first to the other side of sheet to accumulate in the chamber under increased pressure prior to passing out to the other side of the sheet.

21 Claims, 1 Drawing Sheet

FABRIC OF COTTON/NYLON AND ELASTOMERIC NEOPRENE

This application is a continuation of application Ser. No. 07/934,620 filed Aug. 27, 1992.

The present invention relates to a novel fabric.

Insulating fabrics are known which comprise an impermeable, thermally efficient sheet material such as neoprene rubber. Such fabrics are, however, not wearable next to the user's skin for extended periods of time, mainly due to the interference they can cause to the natural biological functions of the skin, in particular perfusion of the skin with oxygen and removal of natural excretions such as water vapour, salt, urea and carbon dioxide.

Previous efforts to improve the wearability of impermeable materials have included perforation of the material and lamination with a more skin-compatible material such as woven cotton.

British Patent No. 1267712, for example, describes (FIG. 4) a breathable fabric in which a perforated elastomeric sheet is bonded between stretch-fabric sheets. The diameter of the perforations reduces slightly towards the outside of the finished garment to facilitate manufacture.

Such fabrics are reasonably wearable given normal external conditions and the biological functions of the wearer. However, if for example the wearer sweats or warms up during exercise or under stress, or the external temperature or humidity rises or falls, or the fabric becomes soaked with water, or in other abnormal situations, the breathable efficiency of the fabric declines rapidly, which can make the garment extremely uncomfortable or even dangerous to wear. Such poor adaptability has limited the use of breathable elastomeric fabrics, for example for insulating and/or protective garments, for medical or veterinary garments and/or dressings (where the patient's skin may be injured or prolonged close contact with the skin may be required), or for exercise and sports garments where rapid changes of perspiration and other skin functions take place. The present invention aims to provide a breathable fabric which goes at least some way towards overcoming the above disadvantages.

According to the present invention, there is provided a fabric comprising a sheet formed of a substantially impermeable material having perforations provided therethrough, each perforation having at least one relatively wide region and at least one relatively narrow region along its length to define an internal chamber open to a first ("inner") side of the sheet and sufficiently closed to the other ("outer") side of the sheet to permit air passing from the first to the other side of the sheet to accumulate in the chamber under increased pressure prior to passing out to the other side of the sheet.

The expressions "relatively wide" and "relatively narrow" mean that the respective regions are wide and narrow relative to each other. The expression "fabric" includes a fabric portion, and the expression "sheet" includes a sheet portion.

The substantially impermeable sheet may be a unitary sheet or a laminate, and is preferably elastomeric (eg. formed from a rubber such as neoprene rubber). In the case of a laminate, different materials may if desired be used for different lamina so as to provide overall a sheet having the desired properties.

Closure of the chamber to the outer side of the sheet by a relatively narrow region of the perforation, in the resulting condition of the sheet, may be complete or partial, and the materials and/or chamber configuration are suitably chosen so that on stretching and/or bending of the sheet or one or more particular lamina thereof the relatively narrow region opens wider than its resting condition to allow exchange of air between the two sides of the sheet. Stretching/bending so as to cause the relatively narrow region of the perforation to open typically results from the desired build-up of pressure in the camber and/or by movement of the fabric in use.

The arrangement may also suitably be capable of creating a pumping effect in the chamber(s) by the periodic stretching and/or bending of the fabric in use, to assist the exchange of air between the inner and the outer sides of the sheet.

In general, it is preferred that even at its widest stretch the relatively narrow region of the perforation is no more than about 65% of the width of the relatively wide region, and less (most preferably substantially less) in the resting condition of the sheet, e.g. less than about 50%, more preferably less than about 35%, for example less than about 15%, of the width of the relatively wide region in the resting condition of the sheet. Where the sheet is a laminate, different lamina may optionally be of different flexibility, and suitably the lamina including the relatively narrow region of the perforation may be of greater flexibility than the lamina including the relatively wide region, for example through being thinner and/or of a material of greater elasticity.

The sheet may also include perforations of different configuration to those which form a novel feature of the invention, e.g. conventional straight-sided fully open perforations, or tapered perforations such as described in the prior art mentioned above. The sheet may also include unperforated regions.

The fabric may additionally have one or more permeable layers, e.g. of woven material, suitably bonded to the perforated sheet. The fabric is suitably capable of being rolled up for storage or transport.

According to a further feature of the present invention, therefore, there is provided a wearable article, such as a garment or dressing, formed from the novel fabric as defined above, the first side of the sheet formed of the substantially impermeable material suitably being directed to the inner side of the article as worn and the other side of the sheet suitably being directed to the outer side of the article as worn.

Each novel perforation as defined above defines at least one chamber within the sheet at the relatively wide region(s) of the perforation, the chamber(s) communicating to both sides of the sheet. One chamber is typically formed by a depression in that side of the sheet which is closer to the body of the user (the "inner" side), to partially enclose a volume of air directly above the user's skin.

The walls of each relatively wide and/or relatively narrow region of the perforations may suitably be parallel over at least a part of the length of the respective region. The perforations are preferably unbranched.

The perforations and associated chambers are suitably of sufficient size and spacing apart to permit the natural biological functions of the user's skin to continue substantially unhindered over a desired period of time, while permitting a controlled (but not excessive) retention of the user's body heat.

The components of the fabric should be non-toxic, non-irritant and comfortable to wear (in the sense of lightweight, flexible and soft to the touch), as well as being resistant to attack and degradation from all natural by-products of the user's body (e.g. sweat, blood, tissue fluid, urine, pus, and gases such as carbon dioxide).

It is found that fabrics of the present invention retain to a substantial extent the advantageous thermal properties of the impermeable sheet material while permitting to a surprising degree the natural biological functions of the user's skin to continue substantially unhindered.

Without wishing to be bound by theory, it is believed that the fabric of the invention permits the natural excretions to diffuse away from the user's skin and atmospheric oxygen to access the user's skin in an unexpectedly efficient way, because the relatively warm and moist air just above the user's skin collects in the chamber(s). This accumulation enables the air in the chamber(s) to attain a higher humidity, temperature and pressure than would be the case in a more open perforation. When, therefore, the relatively narrow region of the perforation opens due to the factors described above, the expulsion and replenishment of fresh air to the chamber takes place with enhanced speed and efficiency.

In more detail, it is believed that the perforations according to the present invention may mimic to some extent the properties of pores (which in biological systems cause an active or driven diffusion of molecules through a barrier with greater efficiency, for a given open area, than larger holes). However, the diffusion properties of the fabric according to the present invention are surprisingly enhanced. Accordingly, the relatively narrow region of the perforation should ideally not be so open that the perforation begins to function more as a hole than as a pore. This, in general, the diffusion rate should be dependent on the perforation diameter (as for biological pores) and not area (as for holes), and/or edge effects such as so-called "diffusion shells" should (as for pores) play a significant part in creating a relatively sharp concentration gradient immediately outside the perforation.

Fabrics in which the perforated elastomeric sheet is a laminate, the lamina including the relatively narrow region of the perforation being of greater flexibility than the lamina including the relatively wide region, and the relatively narrow region of the perforation lying closed or substantially closed in the resting condition, are particularly preferred. Such fabrics provide substantial protection to the wearer from cold or other external hazards (e.g. water, chemicals, bacteria, air etc), while permitting an enhanced air-exchange efficiency as soon as high levels of wearer activity arise, which cause the perforations to open due to flexing of the fabric and/or the higher temperatures and pressures within the chambers of the fabric. In such fabrics, the perforations may conveniently be interspersed with smaller numbers of other types of perforation according to the present invention and/or other (e.g. conventional) perforations. In one particular form, the perforations according to the present invention open when the vapour pressure of moisture in the chamber(s) reaches saturated vapour pressure.

The fabric of the present invention is preferably arranged to regulate the wearer's skin temperature to normal body temperature (37° C.). This requires that the fabric functions as an insulator below body temperature and as a cooling medium above body temperature. The capacity of the perforations to open above a threshold chamber pressure and/or temperature can be exploited to permit increased evaporative loss due to sweating from the skin surface as the body temperature exceeds 37° C., resulting in a skin temperature reduction through loss of latent heat of vaporisation from the skin. Thus, the fabric acts to cool the skin surface and maintain normal body temperature.

As the body temperature drops to 37° C. the production of sweat causes and hence the cooling effect diminishes. This is seen as a continuous process resulting in the maintenance of homoiothermic biological conditions under varying enviromental temperatures. The effect is more marked when the concentration of perforations is high enough to create conditions of significantly increased evaporation from the skin surface. If the fabric is to be used solely to elevate body temperature (e.g. for the initial treatment of victims of hypothermia), the concentration of perforations should be low enough to satisfy the requirement of sufficient removal of water vapour, but for many other uses the opposing warming (below body temperature) and cooling (above body temperature) effects should be maintained in proper balance depending on the desired end use.

By selecting particular elastomeric materials, particular lamina thicknesses, particular sizes of relatively wide regions of perforations, particular sizes of relatively wide regions of perforations, different concentrations of perforations over the fabric area and/or different arrangements of perforation types over the area of the fabric, the fabric's properties can be adjusted to suit the intended use. Moreover, by careful selection of materials and configuration, the fabric can be made to respond in its "breathability" to variations in external conditions and/or in the user's biological functions, so that to some extent such fabrics can self-regulate their "breathability" and hence automatically control the environment next to the wearer's skin within a pre-set temperature range.

The invention will now be described in greater detail, but without limitation, with reference to the accompanying drawings, in which.

Figure 1:
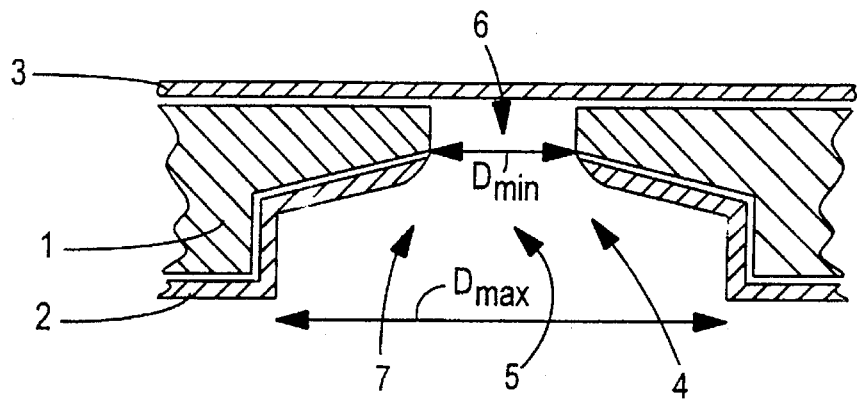
FIG. 1 shows schematically a first fabric in cross-section.

Referring to FIG. 1, the fabric comprises a laminate having a first, thermally efficient, layer 1 of a substantially impermeable sheet material such as neoprene rubber sandwiched between a second layer 2 of a permeable material capable of being worn next to the user's skin (e.g. lightweight four way stretch cotton) and a third, outer, layer 3, also of a permeable material, the nature of which is chosen depending on the use to which the fabric is to be put. The layers are shown slightly spaced apart, for clarity, and the adhesive between adjacent layers has been omitted, for clarity.

The thickness of layer 1 may be chosen to suit the desired application of the fabric. For example, the thickness may be from 0.5–5 mm, suitably from 1–3 mm.

Layers 1 and 2 are perforated by perforation 4, which comprises a relatively wide region 5, on the inner side of layer 1, which tapers to a relatively narrow region 6 on the outer side of layer 1, thereby forming a chamber 7 communicating to both sides of the fabric.

Perforation 4 is generally circular when viewed along its length, and suitably has a minimum diameter $D_{min}$ up to about 10 mm (e.g. from about 0.5 mm to about 10 mm) and a maximum diameter $D_{max}$ approximately 1.5 to 10 (e.g. about 1.5 to about 3) times greater than $D_{min}$. For example, when the thickness of the first layer is 3 mm, $D_{min}$ may be approximately 3 mm and $D_{max}$ may be approximately 10 mm. The centres of adjacent perforations may suitably be from about 10 mm to about 100 mm, typically (in the case of a 3 mm thick first layer) approximately 30 mm, apart and the perforations arranged in a repeating diamond pattern across the fabric.

In the illustrated fabric, perforation 4 has approximately 50% of its length at $D_{max}$, approximately 25% of its length tapering, and approximately 25% of its length at $D_{min}$.

The second layer 2 extends some way up the walls of chamber 7 and guards against chafing or irritation of the user's skin should the fabric be compressed against the user's skin.

The function of the third layer 3 is generally to close the outer end of perforation 4 while permitting air to be exchanged between the user's skin and the outside atmosphere. Where the fabric is intended for domestic use, for example, the third layer may comprise a lightweight permeable material such as lightweight four-way stretch cotton; where the fabric is intended for industrial use, a durable permeable material such as durable nylon could be suitable.

The three layers 1,2,3 are secured together with conventional adhesives (not shown) to form the laminate. Such adhesives are suitably biocompatible, non-toxic, non-irritant and/or resistant to degradation on contact with natural body excretions.

The fabric of FIG. 1 is suitably manufactured by first laminating the second layer 2 to one side of an unperforated first layer 1, and the perforations stamped through the two-layer laminate to form the desired arrangement of perforations and chambers. The stamp head is shaped to correspond with the desired internal configuration of the perforation. The perforations in the fabric illustrated may be formed, for example, by a hollow cylindrical stamp head carrying an external circumferential shoulder, which both cuts through layers 1 and 2 to form region 6 of the perforation and compresses layers 1 and 2 to form region 5. It will be noted that the material from which layers 1 and 2 are formed may require to be sufficiently deformable to permit such stamping, but by synchronising the stamping with the curing (e.g. heat-curing), bonding and/or setting of the adhesive which bonds layers 1 and 2 together and/or by forming the perforations and chambers either before or after modification or treatment of the first layer (e.g. vulcanisation in the case of a rubber such as neoprene), suitably shaped perforations can also be made in elastic materials.

The third layer 3 is subsequently laminated to the other side of the first layer resulting in a triple laminate material with no holes showing on the external surface.

Lamination may be accompanied by the application of vacuum-assisted pressure in inner and outer surfaces of the fabric in conventional manner, before or after the perforations and chambers are created.

Figure 2A:
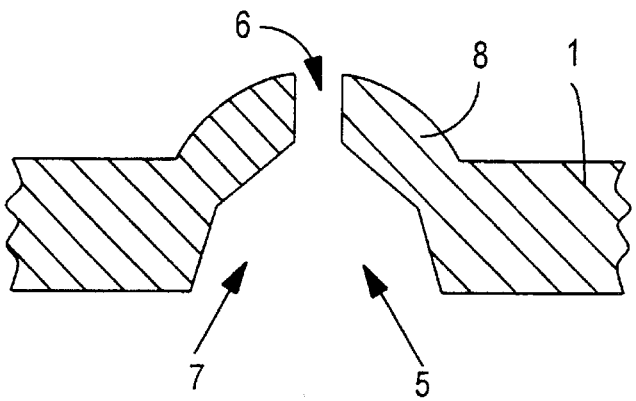
FIG. 2 shows schematically a second fabric in cross-section.

Referring to FIG. 2a, in which like parts are designated as for FIG. 1, a second fabric is shown, made in similar fashion to the fabric of FIG. 1, but in which an outward projection of first layer 1 in the form of a dome 8 surrounds the outer end of the relatively narrow region 6 of the perforation 4.

Figure 2B:
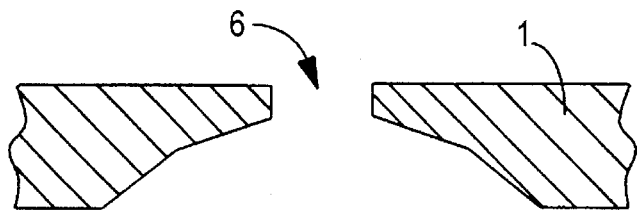

It is found that the efficiency of gas exchange between chamber 7 and the inner and outer sides of the sheet is enhanced in the case of the second fabric, since the stretching and/or bending of the fabric which occurs in use (FIG. 2b) periodically causes the dome 8 to compress downwards, flattening the chamber 7 and causing a pumping effect to more gases into and out of the chamber 7.

Figure 3A:
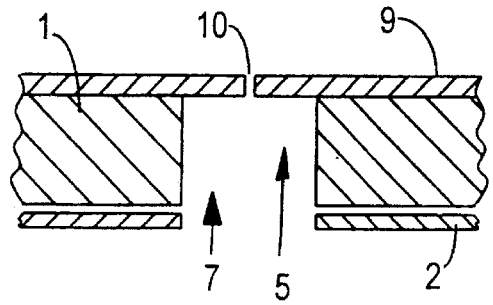
FIG. 3 shows schematically a third fabric in cross-section.

Referring to FIG. 3a, in which like parts are designated as for FIG. 1, a third fabric is shown, made in a rather simpler and cheaper manner than the fabric of FIGS. 1 and 2.

As before, the second layer 2 (e.g. of cotton) is first laminated to one side of the unperforated first layer 1 (e.g. of neoprene), but then parallel-sided perforations are cut through to cut the relatively wide region 5 of a perforation, which will form chamber 7.

Next, a thin membrane 9 (e.g. of latex rubber) is laminated to the outer surface of the sheet to create a drum skin across the outside of the chamber 7. The membrane 9 is then perforated, suitably in the centre, with a small hole 10 which lies closed in the resting condition (FIG. 3a).

Figure 3B:
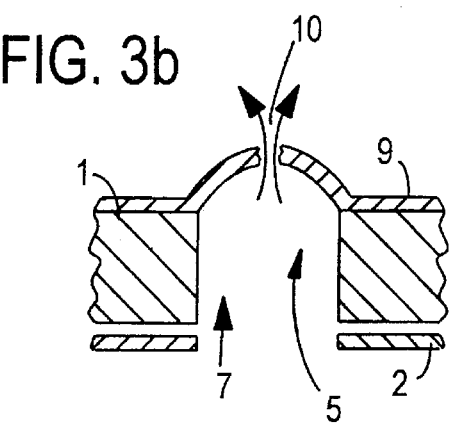

As the temperature increases in the chamber 7 when the fabric is worn, for example when the wearer takes vigorous exercise, the humidity of the chamber 7 and the air pressure will rise resulting in an expansion which will balloon the membrane outward (FIG. 3b), opening the hole 10 (suitably to a maximum diameter of about 1 mm) and allowing the release of air and moisture (as shown by the arrows in FIG. 3b) until stability has been achieved and the membrane 9 will then return to its original state of closure (FIG. 3a). As the air temperature within the chamber rises, the elasticity of the membrane will also increase to facilitate ballooning.

The perforations shown in FIG. 3 are suitably interspersed occasionally with a predetermined number of generally similar perforations but having larger holes (not shown) in the membrane, to allow gaseous exchange and oxygenation of the skin surface when the wearer is at rest, that is when none of the small holes 10 are open. Such fabrics can be constructed to suit the desired use, for example by pre-selecting the material and/or thickness and/or other specifications of the latex membrane 9 so that the holes 10 will not open below a certain temperature, pressure and/or vapour pressure of moisture and the fabric can therefore be "programmed" to function within specific temperatures or other parameters (typically, higher temperature requirements will utilise a relatively thicker membrane 9 and lower temperature requirements a relatively thinner membrane 9), to go at least some way towards creating effectively a thermostatically controlled material to enable different parts of the body which generate more or less heat and/or moisture to be compensated for in the made-up garment.

A suitable external layer (not shown) analagous to layer 3 in FIG. 1 may be provided as desired, but this should not adversely interfere with the ballooning action described above.

In general, with the fabrics of this invention it is preferred to use more smaller perforations rather than fewer larger ones, while of course ensuring that the properties of the fabric are not adversely affected, in order to maximise the rate of active transport of air, moisture etc between one side of the fabric and the other. The number, size and distribution of the perforations, and the extent to which other types of perforations are used in the fabric, should however be selected according to the desired properties of the fabric and its intended use.

The fabric of the invention is lightweight, is an efficient thermal insulator, is comfortable and flexible for extended use, is washable for reusability, is inexpensive, is machinable into garments etc and is sterilisable. By suitable conventional treatment of the external third layer 3 additional advantageous properties such as water, chemical and fire resistance can readily be imparted. By impregnation of the fabric or at least one of the component layers with antibacterial agents or other medicaments, the fabric may readily be adapted for medical and veterinary use.

Medical applications of the fabric include:
i) support fabrics for therapy of injuries and trauma,
ii) post-operative dressings to promote healing by increased vascularisations, e.g. after plastic surgery or skin grafting,
iii) lining fabrics for plaster casts on bone fractures,
iv) fabrics to retain heat and control fluid loss from skin tissues on burns victims,
v) support fabrics and dressings for treatment of periforal vascular disease, rheumatoid arthritis, osteoarthritis, pressure sores, (particularly in care of the elderly), acute hypothermia and osteopathic conditions (e.g. back pain), and
vi) insulating fabrics, e.g. for preventing heat loss in premature babies and trauma victims.

Corresponding veterinary uses are also achievable.

Industrial applications of the fabric include:

i) waterproof clothing, e.g. for fisherman and sailors,
ii) fire-proof clothing, e.g. for oil platform workers and firefighters, and
iii) protective clothing, e.g. for farm workers, construction workers, the rescue services and the military.

Sport and leisure uses of the fabric include:

i) mountaineering clothing,
ii) arctic exploration clothing,
iii) ski clothing,
iv) thermal suits for all sports,
v) sweat suits for fitness and weight-loss exercise, and
vi) suits for sailing.

I claim:

1. A laminated fabric comprising:

(a) a sheet portion of a cotton or nylon material compatible with human skin, said sheet being adhered to (b) a second sheet which is of a substantially water vapor-impermeable thermally insulating elastomeric neoprene material having a multiplicity of formed elongated perforations extending through the thickness of said material, each perforation having a relatively narrow opening in one plane of the material and a relatively wider opening in the opposing plane of said material, each opening, with an associated depression in the material, thereby defining a chamber structure in which a volume of air may accumulate under increased pressure prior to passing through the material out to the other side, said fabric, when worn as a covering over human skin, retaining to a substantial extent the advantageous thermal properties of the impermeable second sheet, while permitting the natural biological functions of the user's skin to continue substantially unhindered.

2. The laminated fabric of claim 1, wherein (b) contains an array of perforations over its surface and associated indentations in the opposite surface wherein the center of one perforation is separated from that of an adjacent one by a distance of about 10 to about 100 mm.

3. The laminated fabric of claim 1, wherein (a) is cotton.

4. The laminated fabric of claim 1 also comprising woven cloth adhered to the (b) second sheet on the plane opposite that to which (a) is adhered.

5. The laminated fabric of claim 1, wherein (b) has a multiplicity of perforations extending through the thickness of said material, each perforation having a diameter of about 0.5 mm to about 10 mm.

6. The laminated fabric of claim 1, wherein (b) has perforations in each of which the narrow opening is up to 65% of the width of the relatively wide opening.

7. The laminated fabric of claim 6, wherein (b) has perforations wherein the narrow opening is less than about 15% of the size of the relatively wide region in the resting condition of the sheet.

8. The laminated fabric of claim 1, wherein the characteristics of sheet (b) of the fabric have been controlled by the selection of at least one of 1) the lamina thickness, 2) the specific size of the relatively wide regions of perforations, 3) the particular concentration of perforations over the area of the sheet, and 4) the different arrangements of perforation types over the area of the sheet.

9. The laminated fabric of claim 1, in which (b) may include unperforated regions.

10. The laminated fabric of claim 1, wherein (b) when covering human skin, exhibits a diffusion rate dependent on at least one of the perforation diameter and the edge effects, said diameter and/or edge effects playing a significant part in creating a relatively sharp concentration gradient immediately outside the perforation.

11. An article of apparel comprising the laminated fabric of claim 1, wherein the wide regions of the perforations and the associated depressions in (b) are located adjacent the skin of the wearer and the narrow regions of the perforations are situated away from the wearer's skin.

12. The article of apparel of claim 11, in which the materials are preselected to function within specific temperature ranges or other parameters, thereby effectively creating a thermostatically controlled environment which compensates for the particular heat and/or moisture generated by different parts of the body.

13. The article of apparel as defined in claim 11 which is able to provide support therapy for injuries and trauma.

14. The article of apparel of claim 11, comprising a plaster cast for bone fractures.

15. The article of apparel of claim 11 adapted to retain heat and to control fluid loss from skin tissue on burn victims.

16. The article of apparel of claim 11 which is useable as waterproof clothing. protection against fire.

17. The article of apparel of claim 11 that provides protection against fire.

18. The article of apparel of claim 11 designed for use in skiing.

19. The article of apparel of claim 11 useable as a sweat suit for exercise.

20. The fabric of claim 1 having three layers, wherein (c) comprises a four-way stretch cotton.

21. The fabric of claim 1 wherein (c) comprises a durable nylon.

* * * * *